United States Patent
Chen et al.

(10) Patent No.: US 9,802,872 B2
(45) Date of Patent: Oct. 31, 2017

(54) METHANATION CATALYST

(71) Applicants: Agency for Science, Technology and Research, Singapore (SG); IHI Corporation, Tokyo (JP)

(72) Inventors: Luwei Chen, Jurong Island (SG); Zhi Qun Tian, Jurong Island (SG); Armando Borgna, Jurong Island (SG); Hiroyuki Kamata, Tokyo (JP); Yoshinori Izumi, Tokyo (JP)

(73) Assignees: AGENCY FOR SCIENCE, TECHNOLOGY AND RESEARCH, Singapore (SG); IHI CORPORATION, Tokyo (JP)

( * ) Notice: Subject to any disclaimer, the term of this patent is extended or adjusted under 35 U.S.C. 154(b) by 0 days.

(21) Appl. No.: 14/779,941

(22) PCT Filed: Mar. 28, 2014

(86) PCT No.: PCT/SG2014/000143
§ 371 (c)(1),
(2) Date: Sep. 24, 2015

(87) PCT Pub. No.: WO2014/158095
PCT Pub. Date: Oct. 2, 2014

(65) Prior Publication Data
US 2016/0052837 A1 Feb. 25, 2016

(30) Foreign Application Priority Data
Mar. 28, 2013 (SG) ............................ 201302358

(51) Int. Cl.
C07C 1/02 (2006.01)
C07C 1/04 (2006.01)
(Continued)

(52) U.S. Cl.
CPC .......... *C07C 1/0435* (2013.01); *B01J 23/755* (2013.01); *B01J 35/002* (2013.01); *B01J 35/008* (2013.01);
(Continued)

(58) Field of Classification Search
CPC .... B01J 23/755; B01J 35/0013; B01J 35/002; B01J 35/0053; B01J 35/008;
(Continued)

(56) References Cited

U.S. PATENT DOCUMENTS 3,962,140 A    6/1976 Alcorn et al.
4,002,658 A *  1/1977 Dalla Betta et al. .. B01J 23/755
                                                      502/337
(Continued)

FOREIGN PATENT DOCUMENTS

CN    101549296 A    10/2009
CN    101607198 A    12/2009
(Continued)

OTHER PUBLICATIONS

Xia, L. et al. Chinese J. Catal. 2011, 32, pp. 1400-1404; Original.*
(Continued)

*Primary Examiner* — Medhanit Bahta
(74) *Attorney, Agent, or Firm* — Choate, Hall & Stewart, LLP

(57) ABSTRACT

The invention relates to use of a catalyst comprising particles of nickel dispersed in a porous silica matrix for catalyzing a methanation reaction. There is also described a method for methanation of a feedstock at least comprising gases carbon monoxide and hydrogen, said method comprising contacting the feedstock with the catalyst.

17 Claims, 7 Drawing Sheets

(51) Int. Cl.
*C07C 1/12* (2006.01)
*B01J 23/755* (2006.01)
*C07C 9/04* (2006.01)
*C10K 3/04* (2006.01)
*C10K 1/32* (2006.01)
*C10G 2/00* (2006.01)
*B01J 37/18* (2006.01)
*B01J 35/00* (2006.01)
*B01J 35/02* (2006.01)
*B01J 35/10* (2006.01)
*C10L 3/08* (2006.01)
*B01J 37/02* (2006.01)

(52) U.S. Cl.
CPC ....... *B01J 35/0013* (2013.01); *B01J 35/0053* (2013.01); *B01J 35/0086* (2013.01); *B01J 35/023* (2013.01); *B01J 35/1019* (2013.01); *B01J 35/1023* (2013.01); *B01J 35/1057* (2013.01); *B01J 35/1061* (2013.01); *B01J 35/1066* (2013.01); *B01J 37/18* (2013.01); *C07C 1/02* (2013.01); *C07C 1/04* (2013.01); *C07C 1/0445* (2013.01); *C07C 1/12* (2013.01); *C07C 9/04* (2013.01); *C10G 2/332* (2013.01); *C10K 1/32* (2013.01); *C10K 3/04* (2013.01); *C10L 3/08* (2013.01); *B01J 37/0203* (2013.01); *B01J 37/0209* (2013.01); *C07C 2521/08* (2013.01); *C07C 2523/755* (2013.01); *C10L 2290/42* (2013.01); *Y02P 20/142* (2015.11)

(58) Field of Classification Search
CPC .. B01J 35/0086; B01J 35/023; B01J 35/1019; B01J 35/1023; B01J 35/1057; B01J 35/1061; B01J 35/1066; B01J 37/18; B01J 37/0203; B01J 37/0209; C07C 1/04; C07C 1/0435; C07C 1/0445; C07C 9/04; C07C 2521/08; C07C 2523/755; C10G 2/332; C10K 1/32; C10K 3/04; C10L 3/08; C10L 2290/42; Y02P 20/142; Y02P 20/52
See application file for complete search history.

(56) References Cited

U.S. PATENT DOCUMENTS

| | | | |
|---|---|---|---|
| 4,071,473 | A | 1/1978 | Atkinson et al. |
| 4,540,714 | A | 9/1985 | Pedersen et al. |
| 4,801,620 | A | 1/1989 | Fujitani et al. |
| 4,833,112 | A | 5/1989 | Przydrozny et al. |
| 5,500,307 | A | 3/1996 | Anzai et al. |
| 5,693,299 | A | 12/1997 | Chopin et al. |
| 2009/0232728 | A1 | 9/2009 | Wagner et al. |
| 2009/0288401 | A1 | 11/2009 | Kaneshiro et al. |
| 2010/0279194 | A1 | 11/2010 | Elangovan et al. |
| 2015/0246347 | A1 | 9/2015 | Miyao et al. |
| 2016/0151765 | A1 | 6/2016 | Kamata et al. |

FOREIGN PATENT DOCUMENTS

| | | |
|---|---|---|
| CN | 101607199 A | 12/2009 |
| CN | 101703933 A | 5/2010 |
| CN | 102949998 A | 3/2013 |
| CN | 102950006 A | 3/2013 |
| GB | 2077613 | 12/1981 |
| JP | S5357194 A | 5/1978 |
| JP | S54-119385 A | 9/1979 |
| JP | S5692826 A | 7/1981 |
| JP | S57-15834 A | 1/1982 |
| JP | S61-161228 A | 7/1986 |
| JP | 62-061640 A | 3/1987 |
| JP | H06-140048 A | 5/1994 |
| JP | H06-226094 A | 8/1994 |
| JP | 2000-126596 A | 5/2000 |
| JP | 2001058130 A | 3/2001 |
| JP | 2004-244246 A | 9/2004 |
| JP | 2007-196206 A | 8/2007 |
| JP | 2008136951 A | 6/2008 |
| JP | 2009-131835 A | 6/2009 |
| JP | 2011-206770 A | 10/2011 |
| JP | 2012-250143 A | 12/2012 |
| SG | 2013050877 A | 1/2015 |
| WO | WO-86/07350 A1 | 12/1986 |
| WO | WO-2010/006386 A2 | 1/2010 |
| WO | WO-2010/143783 A2 | 12/2010 |
| WO | WO-2014/038426 A1 | 3/2014 |
| WO | WO-2014/209237 A1 | 12/2014 |

OTHER PUBLICATIONS

Xia, L. et al. Chinese J. Catal. 2011, 32, pp. 1400-1404; English translation.*
Shi, P. et al. Cat. Lett. 2009, 133, pp. 112-118.*
Sigma-Alrich "SiO2 powder" 2016, pp. 1-3.*
Reucroft, P. J. et al. J. Mat. Energy Systems 1980, 2, pp. 28-33.*
International Search Report for PCT/SG2014/000143, 4 pages (dated Jul. 15, 2014).
Written Opinion for PCT/SG2014/000143, 6 pages (dated Jul. 15, 2014).
Demri, B. and Muster, D., XPS study of some calcium compounds, Journal of Materials Processing Technology, 55:311-314 (1995).
Harada, T. et al., Dai 105 Kai CatSJ Meeting Toronkai A Yokoshu, 133 (Mar. 24, 2010).
International Search Report for PCT/SG2014/000311, 4 pages (dated Oct. 7, 2014).
Kempegowda, R. et al., High temperature desulfurization over nano-scale high surface area ceria for application in SOFC, Korean J. Chem. Eng., 25(2):223-230 (2008).
Ma, Y. et al., A sulfor-tolerant Pd/CEO2 catalyst for methanol synthesis from syngas, Journal of Natural Gas Chemistry, 17:387-390 (2008).
Ma, Y. et al., Methanol synthesis from sulfur-containing syngas over Pd/CeO2 catalyst, Applied Catalysis B: Environmental, 90:99-104 (2009).
Misaka, T. et al., Dai 106 Kai CatSJ Meeting Toronkai A Yokoshu, 74 (Sep. 15, 2010).
Razzaq, R. et al., Catalytic Methanation of CO and CO2 in Coke Oven Gas over Ni—Co/ZrO2—CeO2, Ind. Eng. Chem. Res., 52: 2247-2256 (2013).
Rostrup-Nielsen, J., Chemisorption of Hydrogen Sulfide on a Supported Nickel Catalyst, Journal of Catalysis, 11:220-227 (1968).
Wang, H. et al., Catalytic methanol decomposition to carbon monoxide and hydrogrn over Pd/CeO$^2$—ZrO$^2$—La$^2$O$^3$ with different Ce/Zr molar ratios, Journal of Natural Gas Chemistry, 18:211-216 (2009).
Written Opinion for PCT/SG2014/000311, 9 pages (dated Oct. 7, 2014).
Zyryanova, M.M. et al., Design, scale-out, and operation of a preferential CO methanation reactor with a nickel-ceria catalyst, Chem. Eng. J., 176-117: 106-113 (2011).
Che, M. et al., Nucleation and Particle Growth Processes Involved in the Preparation of Silica-Supported Nickel Materials by a Two-step Procedure, Journal of American Chemical Society, 117(7): 2008-2018 (1995).
Li, X. et al., Effect of Supports on Catalytic Performance of Nickel-Based Catalyst for Methanation, Chinese Journal of Catalysis, 32(8): 1400-1404 (2011).

* cited by examiner

METHANATION CATALYST

INCORPORATION BY CROSS REFERENCE

The present patent application is a U.S. National Stage entry of International Application No. PCT/SG2014/000143, entitled "Methanation Catalyst", filed on Mar. 28, 2014, which claims the benefit of priority from Singapore patent application SG 201302358-5, the entire contents of each of which are hereby incorporated by reference in their entirety herein.

FIELD

The invention deals with methanation catalysts.

BACKGROUND

Substitute natural gas can be produced by a nickel-catalysed methanation reaction using the effluent from a coal/biomass gasification process. However, compounds of sulfur can severely poison nickel catalysts and are often unavoidable in the effluent (commonly up to 5000 ppm) since sulfur is a component of most coal supplies. When nickel is immobilised on an aluminium oxide substrate for use as a catalyst, it is necessary to remove substantially all of the sulfur contained in the feed gas before allowing it to enter the methanator. In particular, it is necessary to reduce the sulfur content of the feed gas to a level of less than about 0.1 ppm, since sulfur poisons the nickel catalyst if it is present in any higher concentration. The gas cleaning process to remove sulfur down to 0.1 ppm imposes additional capital and processing costs. Therefore, there is a need for a nickel catalyst possessing a higher sulfur tolerance than $Ni/Al_2O_3$ so as to minimise the costs of substitute natural gas production.

It is an object of the invention to at least partially satisfy the above need.

SUMMARY OF INVENTION

In a first aspect of the invention there is provided a catalyst comprising particles of nickel dispersed in a porous silica matrix, when used for catalysing a methanation reaction.

The present invention also encompasses the use of a catalyst comprising particles of nickel dispersed in a porous silica matrix for catalysing a methanation reaction.

The following options may be used in conjunction with the first aspect either individually or in any suitable combination.

The porous silica matrix of the catalyst may have pores of about 1 to about 100 nm diameter. The particles of nickel may comprise particles of nickel oxide. The particles of nickel oxide may have a mean particle diameter of about 2 to about 10 nm before being reduced under an atmosphere comprising hydrogen. The particles of nickel may comprise particles of metallic nickel. The particles of metallic nickel may have a mean particle diameter of about 2 to about 10 nm. The catalyst may be particulate. The catalyst may have a sheet-like structure. The catalyst particles may have an aspect ratio of at least about 10, wherein the aspect ratio refers to a ratio of length to thickness of sheets of the sheet-like structure.

The catalyst may comprise a plurality of particles of nickel dispersed therein, wherein the nickel particles may be metallic nickel particles.

The catalyst may have a BET surface area of at least about 200 $m^2/g$. It may have a BET surface area of about 200 to about 1000 $m^2/g$. The catalyst may be porous. The pores of the catalyst, and/or of the silica matrix, may extend continuously from an outside surface of the silica matrix to an outside surface of the nickel. This may allow a reactant or other species to penetrate through the silica matrix to the surface of the nickel.

The catalyst may comprise about 16 wt % to about 63 wt % metallic nickel. The catalyst may comprise about 20 wt % to about 80 wt % nickel oxide. The catalyst may comprise about 20 wt % to about 80 wt % nickel oxide before being reduced under an atmosphere comprising hydrogen. The catalyst may have an active nickel surface area of about 50 to about 160 $m^2/g·Ni$. The term "active nickel surface area" refers to the area of the nickel after the nickel oxide has been reduced and is therefore accessible to hydrogen or reactant gases. The term 'metallic nickel' refers to nickel in its elemental state (i.e., Ni(0)).

In an embodiment there is provided a catalyst when used for catalysing a methanation reaction, said catalyst comprising a plurality of particles of metallic nickel dispersed in a porous silica matrix, wherein the porous silica matrix has pores that extend continuously from an outside surface of the silica matrix to an outside surface of the nickel.

In another embodiment there is provided a catalyst when used for catalysing a methanation reaction, said catalyst comprising a plurality of particles of metallic nickel dispersed in a porous silica matrix, wherein the porous silica matrix, or the catalyst, has a BET surface area of at least about 200 $m^2/g$.

In a further embodiment there is provided a catalyst when used for catalysing a methanation reaction, said catalyst comprising a plurality of particles of metallic nickel dispersed in a porous silica matrix, wherein the catalyst comprises about 13 to 63 wt % nickel and has an active nickel surface area of about 50 to about 160 $m^2/g·Ni$.

The invention also encompasses the use of a catalyst comprising particles of metallic nickel dispersed in a porous silica matrix, e.g., use of a catalyst according the first aspect, for catalysing a methanation reaction, e.g. of a feedstock comprising carbon monoxide and hydrogen, and optionally also comprising a sulfur-containing gas.

In a second aspect of the present invention there is provided use of a catalyst comprising particles of nickel dispersed in a porous silica matrix, e.g., use of a catalyst according the first aspect, for reducing the carbon monoxide content of a gas mixture comprising carbon monoxide and hydrogen.

In an embodiment of the second aspect, the catalyst comprises particles of metallic nickel dispersed in a porous silica matrix.

In a third aspect of the present invention there is provided a method for methanation of a feedstock comprising carbon monoxide and hydrogen. This method comprises contacting the feedstock with a catalyst comprising particles of nickel dispersed in a porous silica matrix, e.g., with a catalyst according the first aspect.

In an embodiment of the third aspect, the catalyst comprises particles of metallic nickel dispersed in a porous silica matrix.

The following options may be used in conjunction with the third aspect either individually or in any suitable combination.

The feedstock may additionally comprise carbon dioxide gas. It may comprise coal gasification effluent and/or biomass gasification effluent. It may additionally comprise a sulfur-containing gas. The sulfur-containing gas may be present at a concentration of over 0.1 ppm, or of about 0.1 to about 5000 ppm. It may comprise hydrogen sulfide, carbonyl sulfide, sulfur dioxide, one or more organic thiols and/or some other sulfur containing gas. The molar ratio of hydrogen to carbon monoxide in the feedstock may be between about 4:1 and about 1:1.

The contacting may comprise passing the feedstock over and/or through and/or past the catalyst, e.g., through a packed bed reactor comprising the catalyst. The pressure of the feedstock during said contacting may be between about 0.5 and about 40 bar. The flow rate of the feedstock may be between about 1000 $h^{-1}$ and 100 000 $h^{-1}$.

The contacting may be conducted at a temperature of at least about 250° C., e.g., at a temperature of between about 250 and about 800° C. The temperature and feedstock flow rate during the contacting may be sufficient to achieve equilibrium conversion from carbon monoxide to methane.

The catalyst may be effective without regeneration after use in the method for at least 2000 minutes using a feedstock having at least about 20 ppm of a sulfur containing gas.

In an embodiment there is provided a method for methanation of a feedstock comprising carbon monoxide and hydrogen, the method comprising contacting the feedstock with a catalyst comprising a plurality of particles of metallic nickel dispersed in a porous silica matrix, wherein the porous silica matrix has pores that extend continuously from an outside surface of the silica matrix to an outside surface of the metallic nickel.

In another embodiment there is provided a method for methanation of a feedstock comprising carbon monoxide and hydrogen, the method comprising contacting the feedstock with a catalyst comprising a plurality of particles of nickel dispersed in a porous silica matrix, wherein the feedstock additionally comprises a sulfur-containing gas present at a concentration of at least about 0.1 ppm, e.g., at about 0.1 to about 5000 ppm.

In another embodiment there is provided a method for methanation of a feedstock comprising carbon monoxide and hydrogen, the method comprising passing the feedstock through a packed bed reactor comprising a catalyst comprising a plurality of particles of nickel dispersed in a porous silica matrix at a flow rate of between about 1000 $h^{-1}$ and about 100 000 $h^{-1}$ wherein the pressure and temperature during said passing are between about 0.5 and about 40 bar and between about 250 and about 800° C. respectively.

In a further embodiment there is provided a method for methanation of a feedstock comprising carbon monoxide, hydrogen, water (steam), methane and carbon dioxide and additionally comprising a sulfur containing gas present at a concentration of at least 0.1 ppm, optionally at least about 20 ppm, wherein the method comprises contacting the feedstock with a catalyst comprising a plurality of particles of nickel dispersed in a porous silica matrix and wherein the catalyst remains effective without regeneration after use in the method for at least 2000 minutes.

In yet a further embodiment there is provided a method for methanation of a feedstock comprising carbon monoxide and hydrogen and additionally comprising a sulfur containing gas at a concentration of at least about 0.1 ppm, optionally at least about 20 ppm, the method comprising passing the feedstock through a packed bed reactor comprising a catalyst comprising a plurality of particles of nickel dispersed in a porous silica matrix and having pores that extend continuously from an outside surface of the silica matrix to an outside surface of the nickel, at a flow rate of between about 1000 $h^{-1}$ and 100 000 $h^{-1}$ wherein the pressure and temperature during said passing are between about 0.5 and about 40 bar and between about 250 and about 800° C. respectively.

In another aspect there is provided a method for conversion of carbon monoxide and hydrogen to methane in the presence of a sulfur containing gas, said method comprising contacting the carbon monoxide and hydrogen with a catalyst comprising particles of nickel dispersed in a porous silica matrix, e.g., with a catalyst according the first aspect.

In a further aspect there is provided a method for reducing the carbon monoxide content of a gas mixture comprising carbon monoxide and hydrogen, said method comprising exposing the gas mixture to a catalyst comprising particles of nickel dispersed in a porous silica matrix. The gas mixture may comprise a sulfur containing gas.

In a further aspect there is provided a method for reducing the carbon monoxide content of a gas, said method comprising adding hydrogen to said gas to form a gas mixture and exposing the gas mixture to a catalyst comprising particles of nickel dispersed in a porous silica matrix. The gas may comprise a sulfur containing gas.

DEFINITIONS

Figure 1:
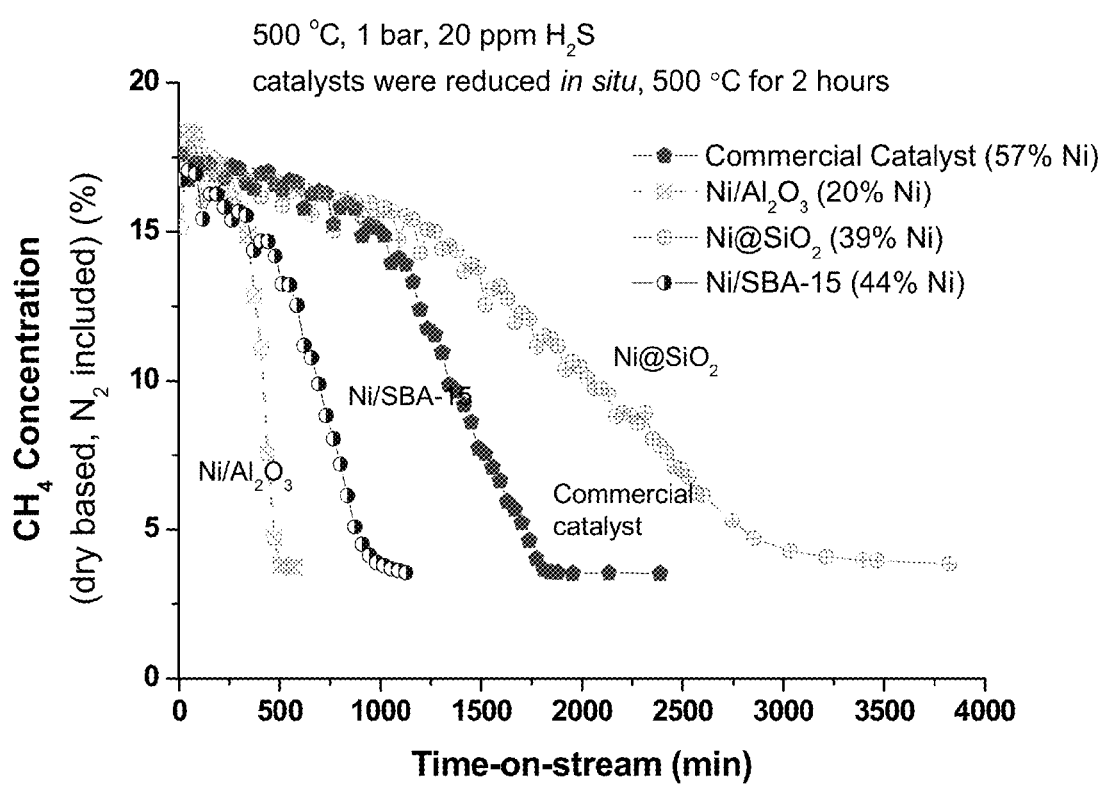
FIG. 1 is a graph illustrating the long-term stability test of catalysts. The graph shows alterations of the methane concentrations with time-on-stream. The feed composition used was: 10% $H_2O$, 10% $N_2$, 40% $H_2$, 20% CO, 16% $CO_2$, 4% $CH_4$, 20 ppm $H_2S$; T=500° C.; GHSV=20,000 $h^{-1}$. All the catalysts were reduced at 500° C. in 50% $H_2/N_2$ for 2 h.

As used in this application, the singular form "a", "an" and "the" include plural references unless the context clearly dictates otherwise. For example, the phrase "a catalyst" also includes a plurality of catalysts.

As used herein, the term "comprising" means "including." Variations of the word "comprising", such as "comprise" and "comprises," have correspondingly varied meanings. Thus, for example, a gas mixture "comprising" carbon monoxide and hydrogen may consist exclusively of carbon monoxide and hydrogen or may include one or more additional components (e.g., carbon dioxide, water vapour, molecular nitrogen, methane, etc.).

As used herein the term "plurality" means more than one. In certain specific aspects or embodiments, a plurality may mean 2, 5, 10, $10^3$, $10^6$, $10^9$, $10^{12}$, $10^{15}$, $10^{18}$, $10^{21}$, $10^{23}$, $10^{24}$, or more, and any integer derivable therein, and any range derivable therein.

It will be understood that use the term "about" herein in reference to a recited numerical value includes the recited numerical value and numerical values within plus or minus ten percent of the recited value unless otherwise specified.

It will be understood that use of the term "between" herein when referring to a range of numerical values encompasses the numerical values at each endpoint of the range. For example, a molar ratio of molecular hydrogen to carbon monoxide in the feedstock of between about 4:1 and about 3:1 is inclusive of a molar ratio of molecular hydrogen to carbon monoxide of 4:1 and a molar ratio of molecular hydrogen to carbon monoxide of 3:1.

Any description of prior art documents herein, or statements herein derived from or based on those documents, is not an admission that the documents or derived statements are part of the common general knowledge of the relevant art.

For the purposes of description all documents referred to herein are hereby incorporated by reference in their entirety unless otherwise stated.

DESCRIPTION OF EMBODIMENTS

The following description conveys exemplary embodiments of the present invention in sufficient detail to enable those of ordinary skill in the art to practice the present invention. Features or limitations of the various embodiments described do not necessarily limit other embodiments of the present invention or the present invention as a whole. Hence, the following detailed description does not limit the scope of the present invention, which is defined only by the claims.

The present invention relates to use of a nickel-based methanation catalyst, Ni@SiO$_2$, which has improved sulfur resistance in methanation reactions. The terminology Ni@SiO$_2$ indicates metallic nickel encapsulated in silica. The present invention also relates to a method for the methanation of a feedstock comprising contacting the feedstock with the Ni@SiO$_2$ catalyst.

The present inventors have identified a nickel-based catalyst (Ni@SiO$_2$) that is able to catalyse the methanation reaction in the presence of sulfur, a common contaminant in coal gasification effluent streams. Experimental evidence suggests the Ni@SiO$_2$ of the present invention is able to outperform the commercial catalyst and significantly outperform other catalysts comprising nickel immobilised on a solid support (Ni/Al$_2$O$_3$ and Ni/SBA-15) when catalysing a methanation reaction in the presence of sulfur. Further, although the nickel content of the Ni@SiO$_2$ is about equal to, or less than, the nickel content of Ni/SBA-15 and the commercial catalyst, Ni@SiO$_2$ maintains a higher level of catalytic activity for longer during exposure to a feedstock comprising hydrogen sulfide. The superior performance of the Ni@SiO$_2$ of the present invention is thought to be due to the improved sintering resistance of the nickel particles protected by the porous SiO$_2$, the structure of which results from the synthesis method employed.

The methanation reaction involves the generation of methane from a feedstock comprising carbon monoxide and hydrogen. The associated exothermic chemical transformation is:

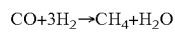

The methanation reaction above is the reverse reaction of steam reforming of methane.

Additionally, in the presence of carbon dioxide, the methanation reaction may also generate methane via:

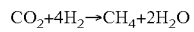

Catalyst

The Ni@SiO$_2$ catalyst of the present invention comprises particles of nickel dispersed in a porous silica matrix. The nickel particles may be metallic nickel particles. The porous silica matrix may have pores of about 1 to about 100 nm in diameter, or about 1 to 50, 1 to 20, 1 to 10, 2 to 10, 5 to 20, 10 to 20, 10 to 50, or 20 to 50 nm in diameter, e.g., about 1, 2, 3, 4, 5, 10, 15, 20, 25, 30, 35, 40, 45, 50, 60, 70, 80, 90 or 100 nm in diameter. Silica pore size and distribution can be determined by those skilled in the art using, for example, nitrogen or hydrogen adsorption/desorption methods. The nickel particles dispersed in the porous silica matrix may have a mean particle diameter of about 2 to about 10 nm, or about 2 to 5, 5 to 10 or 3 to 7 nm, e.g., about 2, 3, 4, 5, 6, 7, 8, 9 or 10 nm. In the event that the nickel particles are not spherical, the diameter of a particle may be taken as the hydrodynamic diameter, or may be take to be the minimum dimension of a particle (e.g., a thickness) or the maximum dimension of a particle (e.g., a length) or the mean dimension of a particle. The particle diameter of the nickel particles may be determined using well-established techniques including transmission electron microscopy and X-ray powder diffraction. The shape of the nickel particles and of the catalyst particles may, independently, be spherical, acicular, flat, flaky, prismoidal, polyhedral, fibrous, irregular, spheroidal, or granular. The pores of the Ni@SiO$_2$ catalyst may extend continuously from an outside surface of the porous silica matrix to an outside surface of the nickel. This may allow gases such as the carbon monoxide and hydrogen gas reactants to penetrate through the encapsulating silica to the surface of the nickel.

The nickel particles may be dispersed, optionally evenly or homogeneously dispersed, throughout the porous silica matrix such that each particle of catalyst comprises a plurality of particles of nickel dispersed therein. The catalyst may comprise about 20 to about 80 wt % nickel oxide, or about 20 to 30, 30 to 40, 40 to 50, 50 to 60, 40 to 60, 60 to 70, 50 to 70, or 70 to 80 wt % nickel oxide, e.g., about 20, 25, 30, 35, 40, 45, 50, 55, 60, 65, 70, 75 or 80 wt % nickel oxide on a weight basis before being reduced under an atmosphere comprising hydrogen. The catalyst may comprise about 16 wt % to about 63 wt % metallic nickel, or about 20 to about 63 wt %, or about 25 to about 63 wt %, or about 30 to about 63 wt %, or about 16 to about 30 wt %, or about 16 to about 55 wt % metallic nickel, or about 16, 20, 25, 30, 35, 40, 45, 50, 55, 60 or 63 wt % metallic nickel. Suitable methods for determining metal content in porous silica are known in the art.

The active nickel surface area of the catalyst may be about 50 to about 160 m$^2$/g·Ni, about 50 to 70, 60 to 80, 60 to 90, 70 to 110, 80 to 120, 90 to 130, 80 to 140, 90 to 150, 90 to 160, 70 to 90 or 75 to 85 m$^2$/g·Ni, e.g., about 50, 55, 60, 65, 70, 75, 80, 85, 90, 95, 100, 105, 110, 120, 130, 140, 150 or 160 m$^2$/g·Ni. When measured using a temperature-programmed desorption of hydrogen method, the active nickel surface area of the catalyst measured at about 500° C. after exposure to hydrogen for about 2 h may be about 40 to about 90 m$^2$/g·Ni, about 50 to about 80 m$^2$/g·Ni, about 60 to about 70 m$^2$/g·Ni, or about 40 to 60, 70 to 90, or 50 to 70 m$^2$/g·Ni, e.g., about 65 m$^2$/g·Ni, or about 40, 50, 60, 70, 80 or 90 m$^2$/g·Ni. Further, the active nickel surface area of the catalyst measured at about 620° C. after exposure to hydrogen for about 15 h may be 75 to about 150 m$^2$/g·Ni, about 85 to about 115 m$^2$/g·Ni, 95 to about 105 m$^2$/g·Ni, e.g., about 100 m$^2$/g·Ni, or about 75, 80, 85, 90, 95, 96, 97, 98, 99, 101, 102, 103, 104, 105, 110, 115, 120 or 125 m$^2$/g·Ni and the active nickel surface area of the catalyst measured at about 750° C. after exposure to hydrogen for about 15 h may be about 55 to about 160 m$^2$/g·Ni, about 65 to about 95 m$^2$/g·Ni, about 75 to about 85, or about 55 to 90 or about 90 to 105, or about 90 to 115, or about 90 to 125, or about 100 to 140, or about 110 to 150, or about 120 to 160 m$^2$/g·Ni, e.g., about 80 m$^2$/g·Ni, or about 65, 70, 75, 76, 77, 78, 79, 81, 82, 83, 84, 85, 90, 95, 100, 110, 120, 130, 140, 150 or 160 m$^2$/g·Ni.

The catalyst, or the porous silica, may have a BET surface area of at least about 200 m$^2$/g, or at least about 300, 400 or 500 m$^2$/g, or from about 200 m$^2$/g to about 600 m$^2$/g, about 200 to 500, 500 to 1000, 300 to 900, 400 to 700, 500 to 700 or 300 to 600 m$^2$/g, or about 200, 300, 400, 500, 600, 700, 800, 900 or 1000 m$^2$/g. The measurement and modeling of a BET equation are methods well known in the art.

In the event that the catalyst particles have a sheet-like structure, they may have an aspect ratio of at least about 10, at least about 12, at least about 15, at least about 20, between about 10 and about 20, between about 10 and about 15, between about 10 and about 30, between about 10 and about 40, between about 20 and about 40, between about 15 and about 25, or about 10, 11, 12, 13, 14, 15, 16, 17, 18, 19, 20, 30, 40, or 50, wherein the aspect ratio refers to the ratio of length to thickness of the sheets of the sheet-like structure.

Catalysis

The catalyst described herein may be used for catalysing a methanation reaction. It may also be used for reducing the carbon monoxide content of a gas mixture comprising carbon monoxide and hydrogen. As noted above, the catalyst is capable of catalysing the conversion of carbon monoxide to methane. This may be useful for generating methane (e.g., for use as a fuel) or for scrubbing carbon monoxide from a feed stream (so as to reduce toxicity) or both.

The catalyst described herein may be used in a method for the methanation of a feedstock comprising gases carbon monoxide and hydrogen, the method comprising contacting the feedstock with the Ni@SiO$_2$ catalyst of the present invention.

The feedstock for input into the claimed method may comprise molecular hydrogen and carbon monoxide, but may additionally comprise carbon dioxide, water vapour, molecular nitrogen, methane, or may additionally comprise a mixture of any two or more of these. The molar ratio of molecular hydrogen to carbon monoxide in the feedstock may be about 4:1, about 3:1, about 2:1, or about 1:1, between about 4:1 and about 3:1, between about 4:1 and about 2:1, between about 4:1 and about 1:1, between about 3:1 and about 2:1, between about 3:1 and about 1:1, or about 4:1, 3.5:1, 3:1, 2.5:1, 2:1, 1.5:1 or 1:1. The ratio may depend on the source of the feedstock. The concentration of carbon monoxide in the gas mixture may be about 10% to about 40%, or about 10 to 30%, 20 to 40% or 20 to 30%, e.g., about 10%, 15%, 20%, 25%, 30%, 35% or 40%. These percentages may be by volume. The feedstock in the present invention may comprise, or may consist essentially of, coal gasification effluent, which is the effluent produced by heating black or brown coal in the presence of oxygen, steam (water vapour) and heat. The feedstock in the present invention may comprise, or may consist essentially of, effluent produced by heating biomass in the presence of oxygen, steam (water vapour) and heat.

The feedstock may also comprise a sulfur-containing gas. The sulfur containing gas may be present at a total concentration of at least about 0.1 ppm, or at least about 0.2, 0.3, 0.4, 0.5, 1, 2, 3, 4, 5, 10, 15, 20, 25, 30, 35, 40, 45, 50, 60, 70, 80, 90, 100, 200, 300, 400, 500, 1000, 1500, 2000, 2500, 3000, 3500, 4000, 4500, or 5000 ppm, or at about 0.1 to about 5000 ppm, or about 1 to about 500 ppm, or about 5 to about 100 ppm, or about 0.1 to 500, 0.5 to 500, 10 to about 100 ppm, or about 10 to about 80 ppm, or about 20 to about 80 ppm, or about 20 to about 100 ppm, or about 10 to about 50 ppm, or about 20 to about 200 ppm, or about 50 to about 300 ppm, or about 100 to about 300 ppm, or about 100 to about 500 ppm, or about 200 to about 600 ppm, or about 300 to about 700 ppm, or about 500 to about 1000 ppm, or about 1000 to about 2000 ppm, or about 1000 to about 3000 ppm, or about 1000 to about 4000 ppm, or about 1000 to about 5000 ppm, or about 2000 to about 3000 ppm, or about 2000 to about 4000 ppm, or about 2000 to about 5000 ppm, or at a total concentration of about 0.1, 0.2, 0.3, 0.4, 0.5, 1, 2, 3, 4, 5, 10, 15, 20, 25, 30, 35, 40, 45, 50, 60, 70, 80, 90, 100, 200, 300, 400, 500, 1000, 1500, 2000, 2500, 3000, 3500, 4000, 4500, or 5000 ppm. The sulfur-containing gas may be hydrogen sulfide, may be carbonyl sulfide, or may be organic thiols (e.g. methane thiol, ethane thiol, thiophenol etc.), or may be an oxide of sulfur, e.g., sulfur dioxide, or may be a mixture of any two or more of these. In the present invention, ppm of a sulfur-containing gas is by volume, i.e. is taken to mean microliters of gas per liter of air (µL/L).

The contacting method may comprise passing the feedstock through a packed bed reactor comprising the catalyst, or over or past a catalyst disposed in a reactor. The reactor may comprise one or more (e.g., 1, 2, 3, 4 or 5) packed reactor beds arranged in series or in parallel. The packed bed reactor or reactors may operate under isothermal or adiabatic conditions. The catalyst may be packed in beds, or in rods, or in plates, or may be coated on the inside surface of a reactor vessel or on some other surface thereof. The catalyst may be coated on any one or more of honeycomb catalyst structures, porous metal catalyst structures, or ceramic matrix catalyst structures. The contacting method may instead comprise bubbling the feedstock through a slurry comprising the catalyst.

During contacting of the feedstock with the Ni@SiO$_2$ catalyst, the feedstock may be at a pressure of about 0.5 to about 40 bar, at least about 0.5 bar, 1 bar, 2 bar, 5 bar, 10 bar, 15 bar, 20 bar, 25 bar, 30 bar, 35 bar or 40 bar or between about 1 and about 2 bar, or between about 1 and 5 bar, 5 and 10 bar, 5 and 20 bar, 10 and 20 bar, 15 and 25 bar, or 15 and 30 bar, or 20 and 40 bar, or 25 and 40 bar, or 30 and 40 bar, or about 0.5, 1, 2, 3, 3.5, 4, 4.5, 5, 6, 7, 8, 9, 10, 15, 20, 25, 30, 35 or 40 bar. The flow rate of the feedstock may be about 20 000 h$^{-1}$, or may be at least about 1000 h$^{-1}$, 5000 h$^{-1}$, or 10 000 h$^{-1}$, or 20 000 h$^{-1}$, or 30 000 h$^{-1}$, or 40 000 h$^{-1}$, or 50 000 h$^{-1}$, or 60 000 h$^{-1}$, or 70 000 h$^{-1}$, or 80 000 h$^{-1}$, or 90 000 h$^{-1}$, or 100 000 h$^{-1}$, or between about 1000 h$^{-1}$ and about 100 000 h$^{-1}$, or between about 1000 h$^{-1}$ and about 10 000 h$^{-1}$, or between about 10 000 h$^{-1}$ and about 50 000 h$^{-1}$, or between about 20 000 h$^{-1}$ and about 60 000 h$^{-1}$, or between about 30 000 h$^{-1}$ and about 70 000 h$^{-1}$, or between about 30 000 h$^{-1}$ and about 80 000 h$^{-1}$, or between about 40 000 h$^{-1}$ and about 90 000 h$^{-1}$, or between about 50 000 h$^{-1}$ and about 100 000 h$^{-1}$, or between about 50 000 h$^{-1}$ and about 80 000 h$^{-1}$, or may be about 1000, 5000, 10 000, 20 000, 30 000, 40 000, 50 000, 60 000, 70 000, 80 000, 90 000, or 100 000 h$^{-1}$. At times, other flow rates may be used. These flow rates may be a space velocity (SV; volumetric flow rate/catalyst volume) or a gas hourly space velocity (GHSV; reactant gas flow rate/catalyst volume). The contacting may be conducted at a temperature of at least about 250° C., or at least about 300, 350, 400, 450, 500, 550 or 600° C., or between about 250 and 800° C., or between about 350 and 600° C., or between about 400 and 500° C., or between about 500 and 800° C., or between about 400 and 600° C., or between about 400 and 700° C., or between about 450 and 550° C., or between about 450 and 650° C., or about 400, 450, 500, 550, 600, 650, 700, 750 or 800° C. The temperature and feedstock flow rate during the contacting method may be chosen to achieve conversion of carbon oxides to methane of at least 50%, at least 60%, at least 70%, at least 80%, or at least 90% of the equilibrium conversion.

The Ni@SiO$_2$ catalyst disclosed herein may remain effective in use without regeneration for at least about 1000 minutes, or at least about 1500, 2000, 2500 or 3000 minutes. It may remain effective for these times when catalysing a methanation reaction using a feedstock comprising at least about 20 ppm of a sulfur containing gas. The term 'effective' here may refer to a reduction in conversion efficiency from its initial value of less than about 20%, or of less than about 15, 10, 5 or 2% over the stated period.

It will be appreciated by persons of ordinary skill in the art that numerous variations and/or modifications can be made to the present invention as disclosed in the specific embodiments without departing from the spirit or scope of the present invention as broadly described. The present embodiments are, therefore, to be considered in all respects as illustrative and not restrictive.

EXAMPLES

The present invention will now be described with reference to specific examples, which should not be construed as in any way limiting.

Example 1: Synthesis and Characterisation of Ni@SiO$_2$ Catalyst

In a typical synthesis of 50 wt % NiO@SiO$_2$, 7.8 g of Ni(NO$_3$)$_2$.6H$_2$O and 10 g of cetyltrimethylammonium bromide (CTAB) were dissolved in 400 mL H$_2$O followed by the addition of 80 mL of NaOH water solution with 4.0 g NaOH by pouring at room temperature. The Ni(OH)$_2$ precipitate capped with CTAB was then collected by centrifugation. The precipitate was dispersed into 320 mL of water to form a suspension. The pH value of the suspension was adjusted to above 12. Subsequently, 7.6 mL of tetraethoxysilane (TEOS) in 80 mL ethanol was slowly dropped into the suspension and maintained at room temperature for 48 h under constant stirring to form a SiO$_2$ shell coated onto the Ni(OH)$_2$ precipitate. After centrifugation, the as received Ni(OH)$_2$ with SiO$_2$ shell was washed thoroughly with deionized water to remove sodium residue in the composite, and dried at 80° C. Finally, 50 wt % NiO@ SiO$_2$ was obtained by calcination in air at 500° C. for 2 h. The as-prepared 50 wt % NiO@SiO$_2$ needs to be reduced in pure or diluted hydrogen gas at a temperature of between 350 and 600° C. for several hours before catalysing the methanation reaction. The Ni content of the resultant Ni@SiO$_2$ catalyst is 39 wt %.

The synthesis of nickel-based Ni@SiO$_2$ catalysts is also described in PCT/SG2013/000472.

The particle size and morphology of pre- and post-reaction Ni@SiO$_2$ were characterised by transmission electron microscopy (TEM, HR-TEM, JEOL JEM-2010F) as discussed below. The crystallization size and phase transformation were determined by X-ray diffraction using a Bruker D8 Advance X-ray diffractometer equipped with Cu K$\alpha$ radiation ($\lambda$=0.154 nm) and in situ X-ray diffraction, respectively, selected results from which are included below. N$_2$ adsorption-desorption isotherms were collected on Micromeritics ASAP 2420 V2.05 (V2.05 J). H$_2$ temperature-programmed reduction (H$_2$-TPR) measurements were carried out with 50 mg of fresh catalysts. Before measurement, the samples were thermally treated under Ar stream at 200° C. for 2 h to remove moisture and other contaminants. The reactor was heated from 30° C. to 850° C. at a rate of 10° C./min in 50 mL/min of 5% of H$_2$/Ar. The hydrogen consumption was monitored using a thermal conductivity detector (TCD) and the results for catalysts Ni@SiO$_2$, commercial catalyst, Ni/SBA-15 are included in the following section.

Example 2: Laboratory Tests of Ni@SiO$_2$ Catalyst Compared to Commercial Catalyst, Ni/SBA-15 and Ni/Al$_2$O$_3$ in the Presence of H$_2$S at 500° C.

Laboratory testing of the long-term stability of the catalyst of the present invention Ni@SiO$_2$, including other catalysts Ni/SBA-15, Ni/Al$_2$O$_3$ and commercial catalyst, under methanation reaction conditions was undertaken using a feedstock comprising 10% H$_2$O, 10% N$_2$, 40% H$_2$, 20% CO, 16% CO$_2$, 4% CH$_4$, and 20 ppm H$_2$S at a temperature of 500° C. and a feedstock flow rate of 20 000 h$^{-1}$.

The results of laboratory tests of Ni@SiO$_2$, commercial catalyst, Ni/SBA-15 and Ni/Al$_2$O$_3$ in catalysing a methanation reaction of this feedstock comprising H$_2$S are shown in FIG. 1, which compares the catalytic performances of commercial catalyst (55% Ni), Ni/SBA-15 (44% Ni) and Ni/Al$_2$O$_3$ (20% Ni) in terms of the concentration of CH$_4$ in the product gas mixture as a function of time-on-stream.

The methane concentrations at the start of the reaction without H$_2$S feeding are around 18 to 20% for the latter three catalysts (commercial catalyst, Ni/SBA-15 and Ni/Al$_2$O$_3$). Obvious deactivation starts over Ni/Al$_2$O$_3$ (20% Ni) when H$_2$S is introduced at the 90$^{th}$ minute, and the activity is completely lost at the 500$^{th}$ minute. The durability of Ni/SBA-15 with 44% Ni content is about the twice of that over 20% Ni/Al$_2$O$_3$. Performances of commercial catalyst (58% Ni) and Ni@SiO$_2$ (39% Ni) are similar and relatively stable at the first 900 minutes of time-on-stream. After 900 minutes, commercial catalysts deactivates with a faster rate than Ni@SiO$_2$. Complete deactivation occurs at around 1800 and 3600 minutes for commercial catalyst and Ni@SiO$_2$, respectively. FIG. 1 clearly indicates the increased durability of Ni@SiO$_2$ over commercial catalyst in the presence of 20 ppm H$_2$S, despite the Ni loading being lower in Ni@SiO$_2$.

Figure 2:
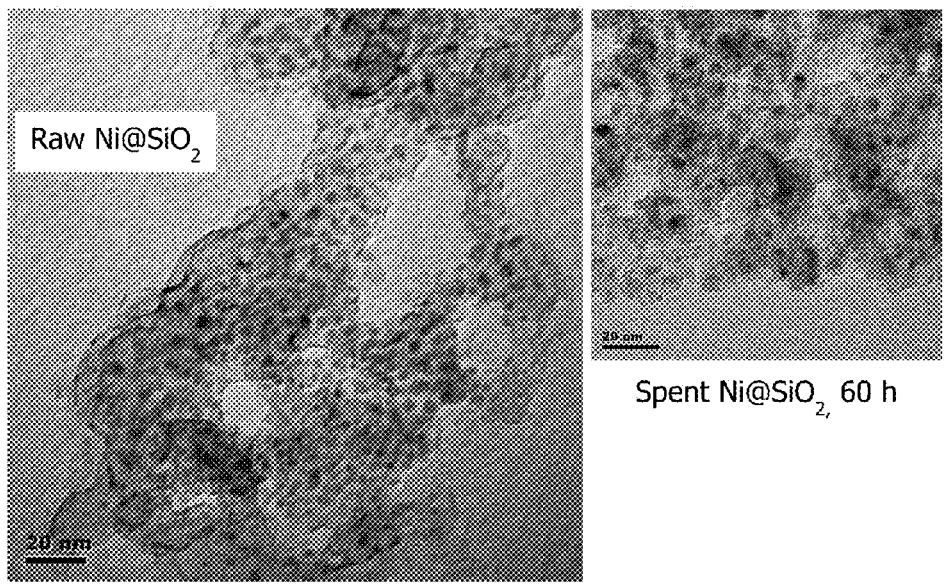
FIG. 2 shows transmission electron microscope images of raw and post reaction Ni@$SiO_2$.
Figure 3:
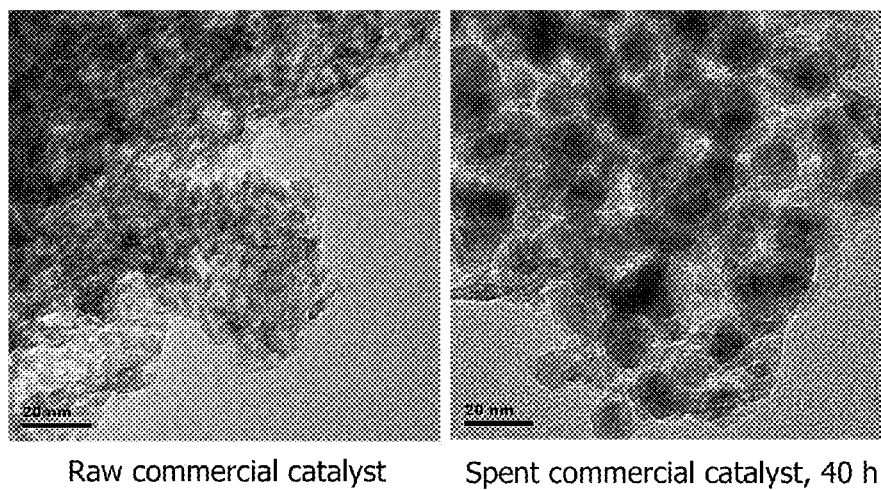
FIG. 3 shows transmission electron microscope images of raw and post reaction commercial catalyst.
Figure 4:
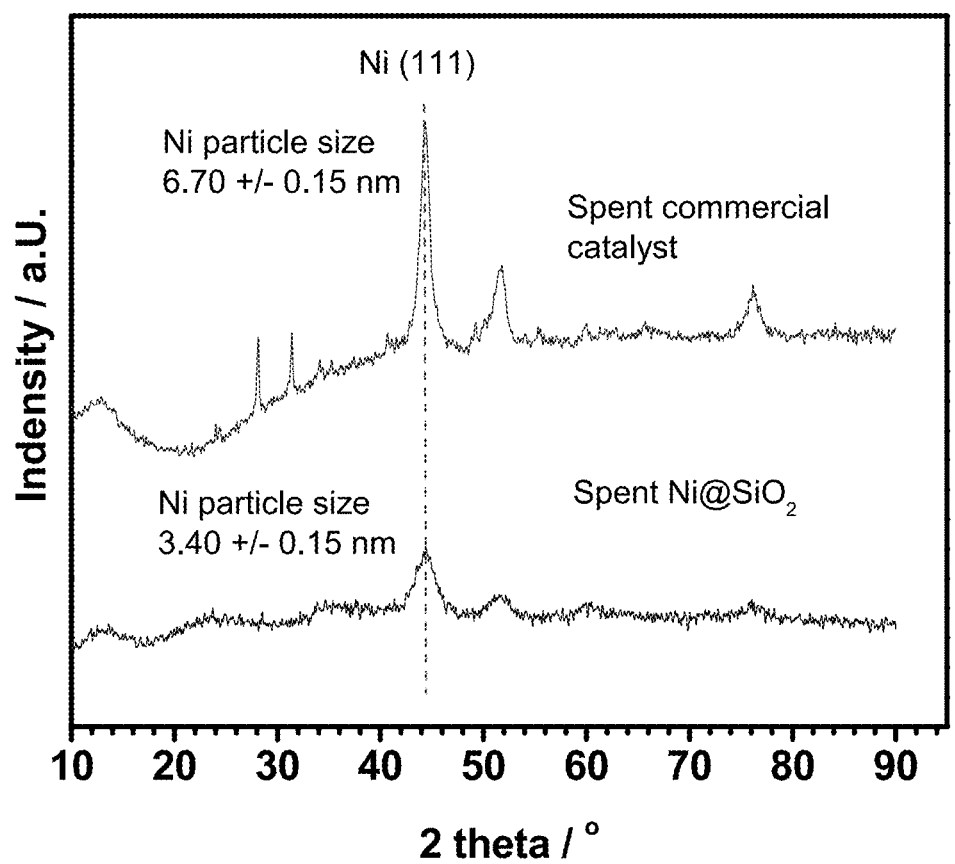
FIG. 4 shows X-ray diffraction (XRD) patterns of spent catalysts Ni@$SiO_2$ and commercial catalyst.

The spent Ni@SiO$_2$ and commercial catalysts were then analysed by TEM and XRD, and results are shown in FIGS. 2 and 3 respectively. The TEM image in FIG. 2 shows that, for the Ni@SiO$_2$ catalyst, the Ni particles in the SiO$_2$ matrix remain small. The TEM image in FIG. 3 shows that, for the commercial catalyst, the Ni particle sizes become larger. The Ni (111) peak in the XRD pattern for spent Ni@SiO$_2$ is visibly broader than the corresponding peak in the XRD pattern for the spent commercial catalyst (FIG. 4). Further, the average Ni particle sizes calculated from these XRD patterns according to Scherrer's equation are 3.4 nm for Ni@SiO$_2$ and 6.7 nm for commercial catalyst. Therefore, TEM and XRD results consistently indicate that Ni@SiO$_2$ is more resistant to sintering than commercial catalyst.

Figure 5:
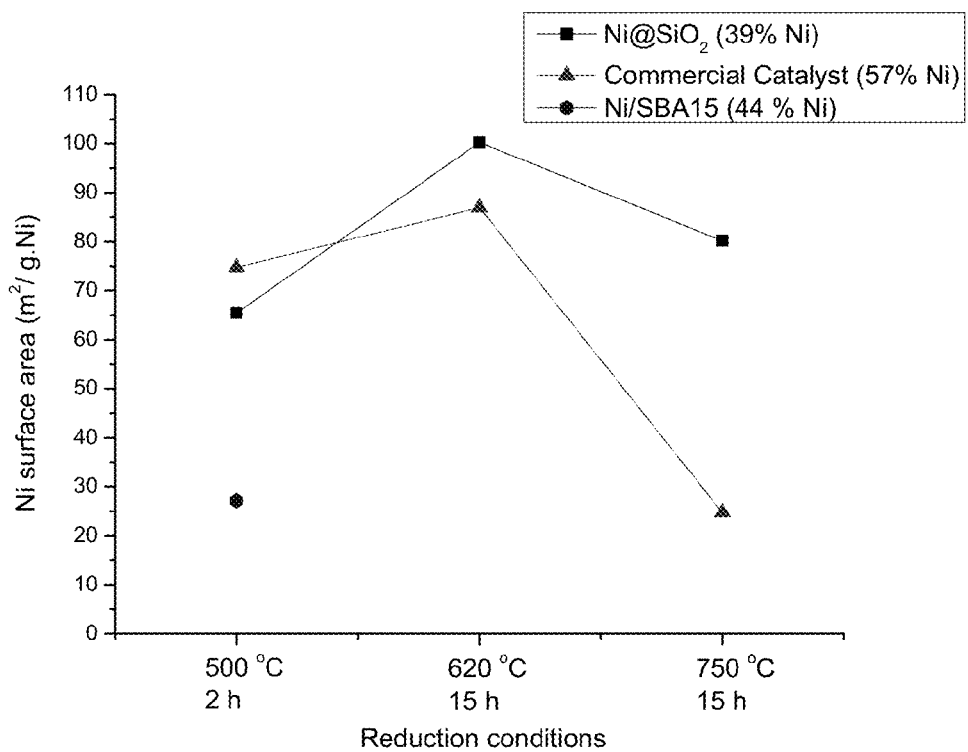
FIG. 5 shows the surface areas of Ni on Ni@$SiO_2$, commercial catalyst and Ni/SBA-15 under various reduction treatments.

The active Ni surface area of Ni@SiO$_2$ (39%), commercial catalyst (57%) and Ni/SBA-15 (44% Ni) were measured by temperature-programmed desorption of hydrogen. Three different reduction conditions were applied, namely 500° C./2 h, 600° C./15 h and 750° C./15 h. As shown in FIG. 5, the Ni surface areas of Ni@SiO$_2$, commercial catalyst and Ni/SBA-15 after being reduced at 500° C. for 2 h are 65.4, 78.4 and 27.2 m$^2$/g·Ni respectively. The areas increase to 90 m$^2$/g (Ni) for both Ni@SiO$_2$ and commercial catalyst when the reduction temperature is increased to 620° C. and the reduction time extended to 15 hours. When the reduction temperature is increased further to 750° C. and 15 hours, the active Ni area of commercial catalyst greatly decreases to 24.7 m$^2$/g·Ni, while the decrease of Ni area in Ni@SiO$_2$ (80.2 m$^2$/g·Ni) is less severe than in commercial catalyst.

Example 3: Laboratory Tests of Ni@SiO$_2$ Catalyst in the Absence of H$_2$S at 500° C.

Figure 6:
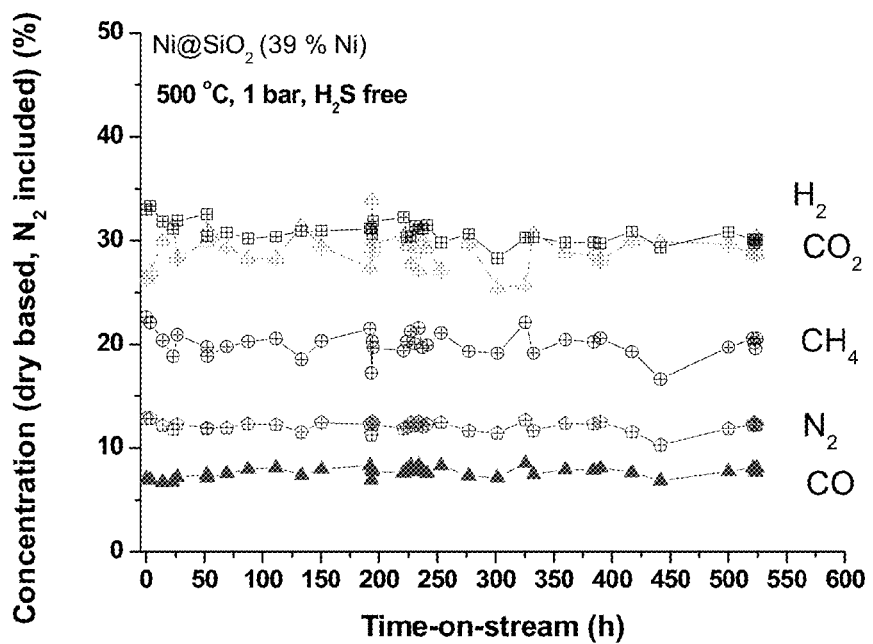
FIG. 6 is a graph illustrating the long-term stability of Ni@$SiO_2$. Concentrations of products (dry based, $N_2$ included) are shown as a function of time-on-stream. The feed composition used was 40% $H_2$, 10% $H_2O$, 20% CO, 10% $CO_2$, 4% $CH_4$, and 10% $N_2$; T=500° C.; P=1 bar; GHSV=20 250 $h^{-1}$. The catalyst has been reduced in 50% $H_2/N_2$ at 500° C. for 2 h.

FIG. 6 displays the results of laboratory tests of Ni@SiO$_2$ in a gas stream under H$_2$S-free conditions, using a feedstock comprising 40% H$_2$, 10% H$_2$O, 20% CO, 16% CO$_2$, 4% CH$_4$, and 10% N$_2$ at 500° C., 1 bar pressure, and a feedstock flow rate of 20 250 h$^{-1}$ showing the concentration of the various catalysis products as a function of time-on-stream. FIG. 6 reveals that in the absence of H$_2$S, the Ni@SiO$_2$ catalyst exhibits very stable activity and lasts for at least 500 h without visible deactivation.

Figure 7:
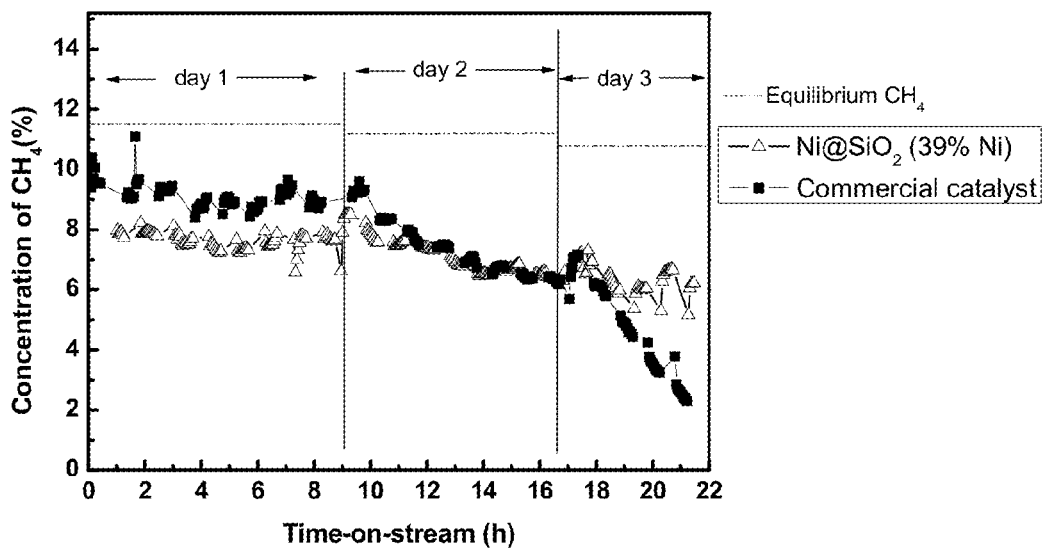
FIG. 7 shows the experimental results obtained using Ni@$SiO_2$ (39% Ni) and commercial catalyst and a coal gasifier outlet gas. Concentration of methane shown as a function of time-on-stream. Reaction conditions: T=485° C., GHSV=50 000 $h^{-1}$. Catalysts have been reduced in 50% $H_2/N_2$ at 600° C. for 2 h.

Example 4: Industrial Test of Ni@SiO$_2$ Catalyst Compared to Commercial Catalyst in the Presence of H$_2$S FIG. 7 shows the experimental results obtained using coal gasification outlet gas from a gasifier facility as feedstock. Two reactors, one containing Ni@SiO$_2$ and the other containing commercial catalyst, were operated for the same time under identical conditions (T=485° C., GHSV=50 000 h$^{-1}$) for three consecutive days. The reaction was stopped at the end of each day and the catalysts were kept in the reactor under the protection of Ar gas overnight. The reactors were heated to the desired reaction temperature under the flow of Ar and the reaction was resumed by reintroducing the outlet gas from the gasifier.

Both catalysts exhibit stable catalytic performance on the first day, producing 9% CH$_4$ and 8% CH$_4$ on average over commercial and Ni@SiO$_2$, respectively. The equilibrium concentration of CH$_4$ should be 11.5%. On the second day, both catalysts start to deactivate gradually with similar deactivation rate. However, commercial catalyst loses its activity very rapidly on the third day test, while Ni@SiO$_2$ seems to maintain a stable deactivation rate as before.

In summary, Ni@SiO$_2$ has shown better catalytic performance for methanation reaction under the gas stream with and without H$_2$S than a bench mark commercial catalyst and other catalysts with similar Ni loading prepared using conventional impregnation method. The superior performance of Ni@SiO$_2$ is due to the improved sintering resistance of Ni protected by porous SiO$_2$.

Example 5: Laboratory Tests of Ni@SiO$_2$ Catalyst Compared to Commercial Catalyst in the Presence of H$_2$S at 500° C.

Laboratory testing of the long-term stability of the catalyst of the present invention Ni@SiO$_2$ (39% Ni) and commercial catalyst (57%), under methanation reaction conditions was undertaken using a feedstock comprising 20% N$_2$, 34.4% H$_2$, 22.9% CO, 18.2% CO$_2$, 4.5% CH$_4$, and 10 ppm H$_2$S at a temperature of 500° C. and a feedstock flow rate of GHSV=36 000 h$^{-1}$. The results are shown in FIG. 8.

Figure 8:
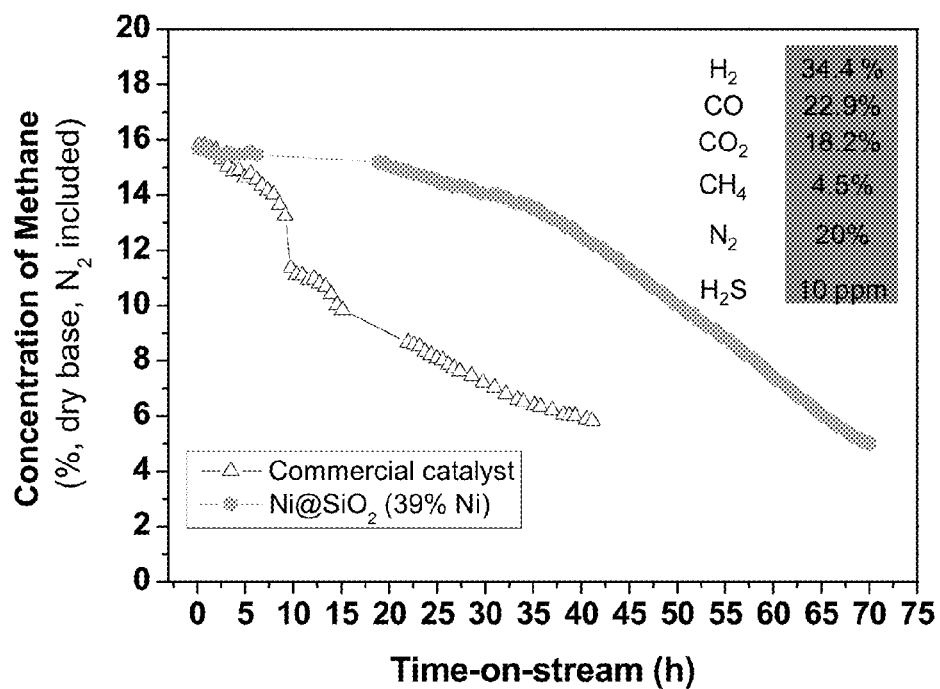
FIG. 8 shows concentration of $CH_4$ (dry based, $N_2$ included) in the product as a function of time-on-stream over commercial (57% Ni) and Ni@$SiO_2$ (39% Ni) catalysts at 500° C., 1 bar and GHSV=36 000 $h^{-1}$. Catalysts have been reduced in 50% $H_2/N_2$ at 600° C. for 2 h.

FIG. 8 shows the concentration of CH$_4$ alteration with time-on-stream over these two catalysts. The present invention Ni@SiO$_2$ (39% Ni) catalyst lasts for about 70 h while the commercial catalyst (57% Ni) can only last for 42 h before becoming completely deactivated.

Example 6: Laboratory Tests of Ni@SiO$_2$ Catalyst Compared to Commercial Catalyst in the Presence of H$_2$S at 600° C.

Laboratory testing of the long-term stability of the catalyst of the present invention Ni@SiO$_2$ (39% Ni) and commercial catalyst (57%), under methanation reaction conditions was undertaken using a feedstock comprising 40% H$_2$, 10% H$_2$O, 20% CO, 16% CO$_2$, 4% CH$_4$, and 10% N$_2$ and 20 ppm H$_2$S at a temperature of 600° C. and a feedstock flow rate of GHSV=20 000 h$^{-1}$. The results are shown in FIG. 9.

Figure 9:
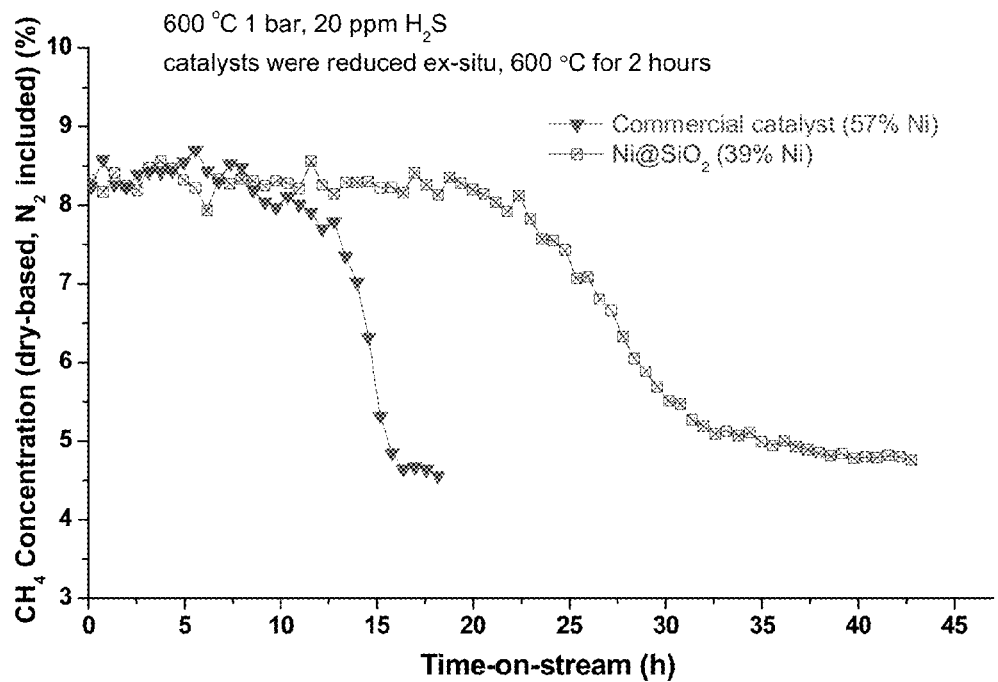
FIG. 9 shows the concentration of $CH_4$ (dry based, $N_2$ included) in the product as a function of time-on-stream over commercial (57% Ni) and Ni@$SiO_2$ (39% Ni) catalysts (10% $H_2O$, 10% $N_2$, 40% $H_2$, 20% CO, 16% $CO_2$, 4% $CH_4$, 20 ppm $H_2S$; T=600° C.; GHSV=20 000 $h^{-1}$.

FIG. 9 shows the concentration of CH$_4$ alteration with time-on-stream over these two catalysts. The present invention Ni@SiO$_2$ (39% Ni) catalyst lasts for about 35 h while the commercial catalyst (57% Ni) can only last for 16 h before completely deactivated.

Example 7: Laboratory Tests of Ni@SiO$_2$ Catalyst in the Absence of H$_2$S at 300° C.

Figure 10:
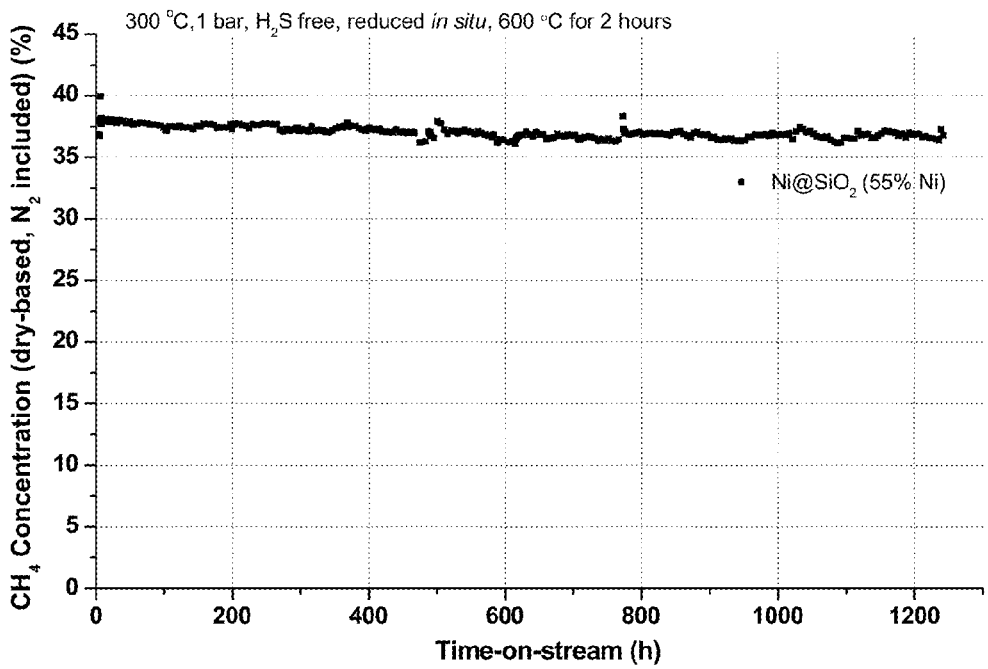
FIG. 10 shows the long-term stability test of Ni@$SiO_2$ (55% Ni) catalyst: Alterations of concentrations of $CH_4$ (dry based, $N_2$ included) in the product with time-on-stream. (GHSV=19,800 $h^{-1}$, 300° C., 1 bar, Gas compositions: 45% $H_2$, 22.5% CO, 18% $CO_2$, 4.5% $CH_4$, 10% $N_2$).

FIG. 10 displays the results of laboratory tests of Ni@SiO$_2$ in a gas stream under H$_2$S-free conditions, using a feedstock comprising 45% H$_2$, 22.5% CO, 18% CO$_2$, 4.5% CH$_4$, and 10% N$_2$ at 300° C., 1 bar pressure, and a feedstock flow rate of 19 800 h$^{-1}$ (GHSV) showing the concentration of the various catalysis products as a function of time-on-stream. FIG. 10 reveals that in the absence of H$_2$S, the Ni@SiO$_2$ catalyst exhibits very stable activity and lasts for at least 1250 h without visible deactivation.

Figure 11:
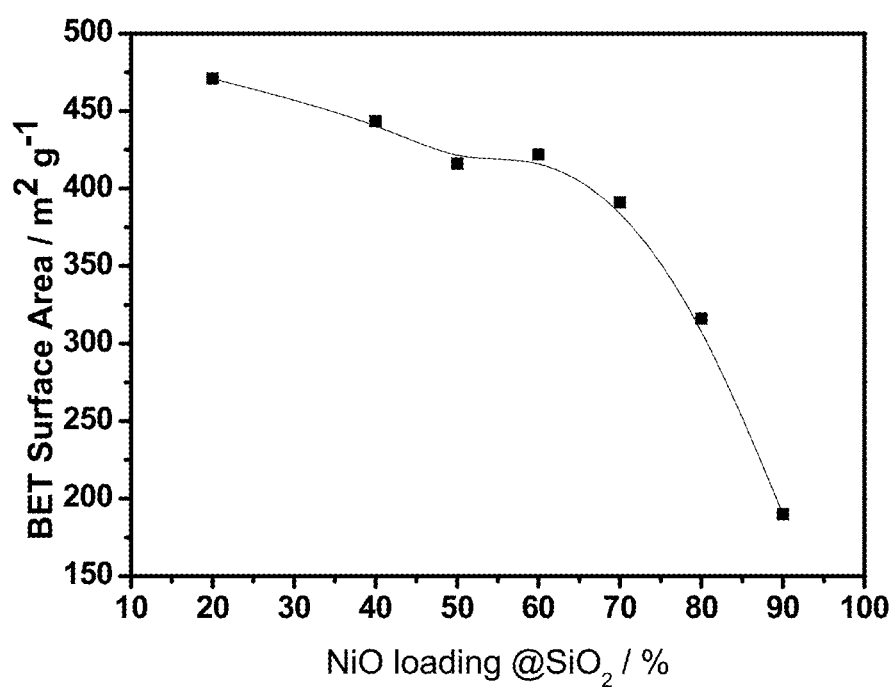
FIG. 11 shows the BET surface area of Ni@SiO$_2$ catalysts with various Ni loadings.

Example 8: Characterization of Catalysts—BET Surface Area and Specific Ni Area The BET surface areas of the present invention Ni@SiO$_2$ catalysts with various NiO contents of 20%, 40%, 60%, 70%, 80% and 90% are compared in FIG. 11. The surface areas decrease with the increment of NiO loadings since the main contributor of the surface area is the porous SiO$_2$. The BET surface area decreases from 475 m$^2$/g from 20% NiO to 375 m$^2$/g of 70% NiO. However, the BET surface area decreases dramatically from 375 m²/g to 175 m²/g when the loading of NiO increases from of 70% to 90%.

The specific Ni area in terms of square meter per gram of catalyst and per gram of Ni of the present invention Ni@SiO$_2$ with various NiO loadings of 40, 50, and 60% as well as the commercial catalyst are tabulated in Table 1. The catalysts have been reduced for 15 h at 620° C. in the flow of pure H$_2$ prior to the H$_2$ adsorption and desorption. The specific Ni area increases with Ni loading and reaches 152.5 m²·g$^{-1}$ Ni for Ni@SiO$_2$ with 47% Ni loading. However, the specific Ni area is only 93.5 m²·g$^{-1}$ Ni for the commercial catalyst with 57% Ni loading. This result clearly indicates that the present invention Ni@SiO$_2$ catalyst has higher Ni utilisation efficiency than the commercial catalyst.

TABLE 1

The specific surface area of Ni after the catalysts have been reduced at 620° C. for 15 hours.

|  | Ni loading (%) | m²/g$_{Cat}$ | m²/g$_{Ni}$ |
| --- | --- | --- | --- |
| 40% NiO@SiO$_2$ | 31 | 37.7 | 120 |
| 50% NiO@SiO$_2$ | 39 | 39.4 | 100.3 |
| 60% NiO@SiO$_2$ | 47 | 71.9 | 152.5 |
| Commercial catalyst | 57 | 52.9 | 93.5 |

The invention claimed is:

1. A method for methanation of a feedstock comprising carbon monoxide and hydrogen, said method comprising contacting the feedstock with a catalyst comprising particles of nickel dispersed in a porous silica matrix, said catalyst comprising about 20 wt % to about 63 wt % metallic nickel, and said catalyst having pores which extend continuously from an outside surface of the silica matrix to an outside surface of the nickel, wherein the active nickel surface area in said catalyst is about 50 m²/g to 160 m²/g Ni.

2. The method of claim 1 wherein the feedstock additionally comprises carbon dioxide gas.

3. The method of claim 1 wherein the feedstock additionally comprises steam.

4. The method of claim 1 wherein the feedstock comprises coal gasification effluent and/or biomass gasification effluent.

5. The method of claim 1 wherein the feedstock additionally comprises a sulfur-containing gas.

6. The method of claim 5 wherein the sulfur-containing gas comprises any one or more of hydrogen sulfide, carbonyl sulfide, sulfur dioxide or an organic thiol.

7. The method of claim 1 wherein the molar ratio of hydrogen to carbon monoxide in the feedstock is between 4:1 and about 1:1.

8. The method of claim 1 wherein the pressure of the feedstock during said contacting is between about 0.5 and about 40 bar.

9. The method of claim 1 wherein said contacting is conducted at a temperature of at least about 250° C.

10. The method of claim 1 wherein the catalyst is effective without regeneration after use in said method for at least 2000 minutes using a feedstock having at least 20 ppm of a sulfur containing gas.

11. The method of claim 1 wherein the porous silica matrix of the catalyst has pores of about 1 nm to 100 nm in diameter.

12. The method of claim 1 wherein the particles of nickel have a mean particle diameter of about 2 nm to 10 nm.

13. The method of claim 1 wherein said catalyst has a BET surface area of at least about 200 m²/g.

14. A method for reducing the carbon monoxide content of a gas mixture comprising carbon monoxide and hydrogen, said method comprising exposing the gas mixture to a catalyst comprising particles of nickel dispersed in a porous silica matrix, said catalyst comprising about 20 wt % to about 63 wt % metallic nickel, and said catalyst having pores which extend continuously from an outside surface of the silica matrix to an outside surface of the nickel, wherein the active nickel surface area in said catalyst is about 50 m²/g to 160 m²/g Ni.

15. The method of claim 14 wherein the gas mixture comprises a sulfur containing gas.

16. A method for reducing the carbon monoxide content of a gas, said method comprising adding hydrogen to said gas to form a gas mixture and exposing the gas mixture to a catalyst comprising particles of nickel dispersed in a porous silica matrix, said catalyst comprising about 20 wt % to about 63 wt % metallic nickel, and said catalyst having pores which extend continuously from an outside surface of the silica matrix to an outside surface of the nickel, wherein the active nickel surface area in said catalyst is about 50 m²/g to 160 m²/g Ni.

17. The method of claim 16 wherein the gas comprises a sulfur containing gas.

* * * * *